United States Patent [19]

Fujita et al.

[11] Patent Number: 4,495,051
[45] Date of Patent: Jan. 22, 1985

[54] GALVANIC CELL TYPE OXYGEN SENSOR

[75] Inventors: Yuko Fujita; Hisashi Kudo; Ikuo Tanigawa, all of Kyoto, Japan

[73] Assignee: Japan Storage Battery Company Limited, Kyoto, Japan

[21] Appl. No.: 538,013

[22] Filed: Sep. 30, 1983

[51] Int. Cl.³ .................. G01N 27/30; G01N 27/54
[52] U.S. Cl. .................. 204/408; 204/414; 204/415
[58] Field of Search .............. 204/415, 414, 408, 1 P, 204/403; 128/635

[56] References Cited

U.S. PATENT DOCUMENTS

| | | | |
|---|---|---|---|
| 3,235,477 | 2/1966 | Keyser et al. | 204/415 |
| 3,258,682 | 6/1966 | Maurer | 204/408 X |
| 3,528,904 | 9/1970 | Cliffgard | 204/415 X |
| 3,926,766 | 12/1975 | Niedrach et al. | 204/415 X |
| 4,132,616 | 1/1979 | Tantram et al. | 204/415 |
| 4,198,280 | 4/1980 | Swartz | 204/415 |
| 4,230,537 | 10/1980 | Delente et al. | 204/415 X |
| 4,252,627 | 2/1981 | Ohashi et al. | 204/415 |

FOREIGN PATENT DOCUMENTS 53891  5/1974  Japan .................. 204/415

OTHER PUBLICATIONS

R. Elsworth, The Chemical Engineer, pp. 63–71, Feb. 1972.

Primary Examiner—G. L. Kaplan
Attorney, Agent, or Firm—Sughrue, Mion, Zinn, Macpeak & Seas

[57] ABSTRACT

A galvanic cell type oxygen sensor comprising a galvanic cell comprised of a cathode made up of metal effective for the electrolytic reduction of oxygen, an anode made up of lead material and an electrolyte made up of an aqueous mixed solution of organic acid and organic acid salt, which has a long life and a high output voltage, is not at all affected by carbon dioxide and which can prevent the generation of hydrogen from the cathode, is disclosed.

4 Claims, 5 Drawing Figures

GALVANIC CELL TYPE OXYGEN SENSOR

FIELD OF THE INVENTION

The present invention relates to a galvanic cell type oxygen sensor and more particularly, to a galvanic cell type oxygen sensor comprising a galvanic cell comprised of a cathode made up of metal effective for the electrolytic reduction of oxygen, an anode made up of lead and an electrolyte, and constructed so that oxygen diffusion to the cathode is limited by a polymer film, and has a thermistor and a resistor connected between the cathode and the anode.

BACKGROUND OF THE INVENTION

There have been known various types of oxygen sensors such as a galvanic cell type sensor (fuel cell type sensor), a polarograph type sensor, a paramagnetic wind type sensor, and a solid zirconia electrolyte type sensor. Of these sensors, the galvanic cell type oxygen sensor is generally simple and cheap and can work at room temperature, so that it is used in wide areas of application.

The galvanic cell type oxygen sensor comprises a galvanic cell comprised of a cathode made up of metal effective for the electrolytic reduction of oxygen such as platinum, gold or silver, an anode made up of lead and an electrolyte, and the sensor makes use of the linear relation between an oxygen concentration and an electric current flowing between the cathode and the anode when a certain resistor is connected between the cathode and the anode.

In the galvanic cell type oxygen sensor, the cathode, the anode and the electrolyte are housed in a cell container. A part of the cell container is made up of a polymer film. This polymer film is partially in intimate contact with the cathode and functions to control appropriately the diffusion rate of oxygen which permeates through the polymer film and reaches the cathode surface.

It is usual that a thermistor for temperature compensation is further connected between the cathode and the anode in addition to the resistor.

The conventional galvanic cell type oxygen sensor had such a fatal defect that its life was as short as 10 to 12 months. The short life of the conventional sensor was caused by use of, as the electrolyte, an aqueous solution of potassium hydroxide or sodium hydroxide.

With a galvanic cell type oxygen sensor employing an alkaline electrolyte, the electrolytic reduction of oxygen as shown in equation (1) occurs at the cathode, whereas the reaction as shown in equation (2) occurs at the anode.

$$O_2 + 2H_2O + 4e^- \rightarrow 4OH^- \quad (1)$$

$$2Pb + 4OH^- \rightarrow 2PbO + 2H_2O + 4e^- \quad (2)$$

PbO that is a reaction product of the anode becomes dissolved into the electrolyte and thus, the surface of the lead electrode is always renewed. In such a state, since the potential of the anode is stabilized, the galvanic cell type oxygen sensor works normally. But when the electrolyte is saturated with the reaction product of the anode, the anode surface is passivated, and the overvoltage of the anode is increased. Thus, the electric current flowing between the cathode and the anode changes, and the linear relation between the oxygen concentration and the electric current breaks down, which results in ending the life of the oxygen sensor.

The reason why the life of the conventional galvanic cell type oxygen sensor employing an alkaline electrolyte was so short resides in that the solubility of PbO as the reaction product in the alkaline electrolyte is so small as about 0.1 mol/l at maximum.

On the other hand, it has been also known that the life of the galvanic cell type oxygen sensor employing an alkaline electrolyte is further shortened when the sensor is placed in an atmosphere containing a relatively high concentration of carbon dioxide. That is because carbon dioxide permeates through the polymer film to be dissolved in the electrolyte and forms insoluble lead carbonate ($PbCO_3$) or basic lead carbonate [$Pb_2CO_3(OH)_2$] instead of PbO formed according to the above equation (2) at the anode, which results in markedly increasing the overvoltage of the anode.

Japanese Patent Application (OPI) No. 53891/1974 discloses that acetic acid can be used as an electrolyte for the galvanic cell type oxygen sensor. The term "OPI" as used herein refers to a "published unexamined Japanese patent application".

When an aqueous solution of acetic acid is used as the electrolyte, the reaction as shown in equation (3) occurs at the cathode, whereas the reaction as shown in equation (4) occurs at the anode.

$$O_2 + 4H^+ + 4e^- \rightarrow 2H_2O \quad (3)$$

$$2Pb + 2H_2O \rightarrow 2PbO + 4H^+ + 4e^- \quad (4)$$

The reaction product of the anode is also PbO as in the case of using the alkaline electrolyte. The solubility of PbO in the aqueous solution of acetic acid is 2.1 mol/l, which is about 20 times larger than that of PbO in the alkaline electrolyte. Therefore, it could be inferred that the oxygen sensor employing an acetic acid solution as the electrolyte has an extremely long life. However, the oxygen sensor employing an acetic acid solution as the electrolyte has not ever been put into practice uses, and there have not been found any literatures about the life of the sensor. This is because the conductivity of the aqueous solution of acetic acid is as small as $16 \times 10^{-4} \Omega^{-1}.cm^{-1}$ at a concentration of 3 mol/l at 18° C., and the internal resistance of the oxygen sensor becomes too high.

Another reason why the acetic acid solution has not been put into practice uses as the electrolyte resides in that there is a possibility that hydrogen generates from the cathode. When the oxygen sensor is placed in an atmosphere having an oxygen concentration near zero, the cathode and the anode have inevitably almost the same potential because they are connected through the resistor. Therefore, unless the potential of the lead anode, i.e., the potential of the cathode, is made nobler than an equilibrium potential of the cathode for hydrogen generation, hydrogen likely generates from the cathode. The equilibrium potential of the cathode for hydrogen generation is provided by equation (5).

$$E_H = -0.2412 + 0.05916 \left( \log \frac{1}{\sqrt{P_{H2}}} - pH \right) \quad (V \text{ vs } SCE) \quad (5)$$

wherein $E_H$ is an equilibrium potential for hydrogen generation at 25° C.; $P_{H2}$ is a partial pressure of hydrogen; and pH is a hydrogen ion concentration in the electrolyte.

In the equation (5), when hydrogen generates in the form of bubbles from the cathode, $P_{H_2}$ equals 1, so that the equation (5) is transformed into equation (6).

$$E_H = -0.2412 - 0.05916 \text{pH} \qquad (6)$$

In the equation (6), the lower the pH, the nobler will become the equilibrium potential of the cathode for hydrogen generation and thus the larger will become the possibility of hydrogen generation from the cathode.

When a solution having a low pH such as an acetic acid solution is used as the electrolyte, the equilibrium potential of the cathode for hydrogen generation becomes very noble, and the hydrogen generation from the cathode occurs almost certainly.

SUMMARY OF THE INVENTION

An object of the present invention is to provide a quite novel galvanic cell type oxygen sensor comprising a galvanic cell comprised of a cathode made up of metal effective for the electrolytic reduction of oxygen, an anode made up of lead and an electrolyte, wherein the galvanic cell is so constructed that oxygen diffusion to the cathode is controlled by a polymer film and a resistor and a thermistor are connected between the cathode and the anode, and the electrolyte consists of an aqueous mixed solution of organic acid and organic acid salt. The galvanic cell type oxygen sensor according to the present invention has a life of 10 to 20 times longer than that of the conventional sensor employing an alkaline electrolyte, is not at all affected by carbon dioxide, has a low internal resistance, and is freed from the hydrogen generation at the cathode.

DETAILED DESCRIPTION OF THE INVENTION

Figure 1:
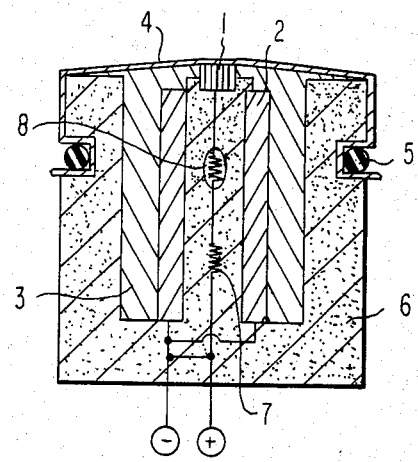
FIG. 1 shows a cross-sectional view of a galvanic cell type oxygen sensor.

The life, internal resistance, durability to carbon dioxide and hydrogen-generation possibility of a galvanic cell type oxygen sensor depend upon an electrolyte used in the sensor.

In order to extend the life of the sensor, it is essential to select an electrolyte having a high solubility against PbO that is a reaction product of the anode. In order to obtain a sufficiently high output voltage, it is necessary to use an electrolyte having a high conductivity. Further, in order to avoid the effect of carbon dioxide, it is necessary to render the electrolyte acidic. Still further, in order to eliminate the possibility of hydrogen generation from the cathode, it is necessary to select an electrolyte in which the equilibrium potential of the cathode for hydrogen generation is poorer than the equilibrium potential of lead as the anode.

Thus, from the viewpoint of the requirements for the electrolyte of a galvanic cell type oxygen sensor, the aqueous alkaline solution has only a defect that the solubility against PbO is low whereas the aqueous solution of acetic acid has a low conductivity and brings about hydrogen generation from the cathode.

We extensively investigated electrolytes for the galvanic cell type oxygen sensor which could meet all the requirements as described above. As the result, we found that an aqueous solution of organic acid and organic acid salt and optionally, lead compound is useful as the electrolyte as demanded.

The organic acid increases the solubility of PbO as a reaction product of the anode and contributes to extension of the life of an oxygen sensor and to elimination of the effect of carbon dioxide on the sensor. Suitable examples of organic acids which can be used include acetic acid, propionic acid and n-butyric acid. As described above, the solubility of PbO in acetic acid is about 20 times that in an aqueous alkaline solution. The solubility of PbO in propionic acid is about 1.5 mol/l and is overwhelmingly high as compared with its solubility of 0.1 mol/l in an alkaline aqueous solution. The solubility of PbO in n-butyric acid shows a value of about 1.0 mol/l, which is of course higher than its solubility in an aqueous alkaline solution.

However, the electrolyte cannot be made up of only the aqueous solution of such organic acid because the solution has a low conductivity and is accompanied by a possibility of hydrogen generation from the cathode. As described above, the conductivity of an aqueous solution of acetic acid having a concentration of 3 mol/l is only $16 \times 10^{-4} \Omega^{-1} \cdot \text{cm}^{-1}$ at 18° C.

On the other hand, the addition of alkali metal or ammonium salt of organic acid to the aqueous solution of organic acid results in a substantial increase in the conductivity. For example, when an aqueous solution of acetic acid having a concentration of 3 mol/l is blended with potassium acetate in an amount of 4 mol/l, the conductivity of the resulting solution is increased to $1250 \times 10^{-4} \Omega^{-1} \cdot \text{cm}^{-1}$. Suitable examples of the alkali metal or ammonium salts of organic acids which can be used include formic acid salt, acetic acid salt, propionic acid salt, n-butyric acid salt, maleic acid salt and glutamic acid salt. Examples of the alkali metals in these organic acid salts include lithium, potassium and sodium.

The alkali metal or ammonium salt of organic acid contributes to the adjustment of the pH of the electrolyte and also as a result, to hindrance of hydrogen generation from the cathode. The pH of an aqueous solution of organic acid is usually 2 to 3, but when an alkali metal or ammonium salt of organic acid is added to the organic acid solution, it is possible to adjust the pH of the mixed solution in the range of 4 to 7. As is clear from the foregoing equation (6), the higher the pH, the poorer will become the equilibrium potential of the cathode for hydrogen generation and the harder will become the occurrence of hydrogen generation. This respect will be described later in more detail.

The excessive addition of the alkali metal or ammonium salt of organic acid to make the pH of the electrolyte higher than 7 must be avoided because it makes it impossible to protect the sensor from the effect of carbon dioxide.

In a mixed solution of the organic acid and the alkali metal or ammonium salt of organic acid, the combination of organic acid and organic acid salt having the same organic acid radical each other decreases the pH change of the electrolyte because of buffer effect, leading to the stabilized output of the oxygen sensor. However, such combination is not always necessary.

Lead compound which is an optional component of the electrolyte of the present invention is further effective for hindering the hydrogen generation from the cathode. In an oxygen concentration region near zero, the cathode and the anode of the oxygen sensor have substantially the same potential because they are connected each other through a resistor. Therefore, if the potential of the lead anode is made nobler, the possibility of hydrogen generation from the cathode can be reduced accordingly. The equilibrium potential of lead is given by the following equation.

$$E_{Pb/Pb^{2+}} = -0.367 + 0.0296 \log [Pb^{2+}] (V \text{ vs SCE}). \quad (7)$$

wherein $E_{Pb/Pb^{2+}}$ is the equilibrium potential of lead at 25° C., and $[Pb^{2+}]$ is an activity of lead ions in the electrolyte.

The more are the amounts of lead ions added, the nobler will become the potential of the lead anode. For example, in an aqueous mixed solution of acetic acid and potassium acetate in amounts of 5 mol/l and 4 mol/l, respectively, the measured potential of the lead anode is about −0.62 V (vs SCE). This value is poorer than the equilibrium potential for hydrogen generation (−0.60 V vs SCE) at the same pH (6.1), so that a small possibility of the hydrogen generation from the cathode remains. However, when lead acetate is added to this electrolyte in an amount of 0.1 mol/l, the measured potential of the lead anode becomes −0.59 V (vs SCE). This potential is nobler than the equilibrium potential for hydrogen generation, so that the hydrogen generation from the cathode cannot at all take place.

As the lead compound which can be added to the electrolyte, lead oxide or any lead salt can be used. As the lead salt, lead salts of organic acids are preferably used. Further, since lead oxide is always formed during use of the galvanic cell type oxygen sensor, there may be a case that the hydrogen generation does not take place even though a lead compound is not particularly added.

As described above, an object of the present invention is to provide a nearly ideal galvanic cell type oxygen sensor which has a long life and low internal resistance, is never affected by carbon dioxide and is freed from a possibility of hydrogen generation from the cathode by adopting as the electrolyte an aqueous mixed solution of organic acid, alkali metal or ammonium salt of organic acid and optionally, lead compound. The organic acid and the alkali metal or ammonium salt of organic acid used in the present invention may each be a single component or mixed components. Further, it is preferable that the electrolyte is gelated with a gelling agent such as a dispersion of silica.

On the other hand, the present invention has another characteristic in the shape of the cathode in addition to the composition of the electrolyte. In an aqueous mixed solution of organic acid and organic acid salt, transfer of electric charges is carried out not only by hydrogen ions (H+) but also by cations dissociated from the organic acid salt. For example, in an aqueous mixed solution of acetic acid and potassium acetate, transfer of electric charges is carrid out not only by hydrogen ions (H+) but also by potassium ions (K+), so that there may be a case that on the cathode surface, the concentration of potassium ions becomes high and the electrolyte becomes locally basic though the bulk of the electrolyte is acidic. If an atmosphere to be detected does not contain carbon dioxide, it is out of the question whether the electrolyte in the vicinity of the cathode surface is basic or acidic. However, in an atmosphere containing carbon dioxide of relatively high concentration, when the electrolyte in the vicinity of the cathode surface becomes basic, insoluble lead carbonate or basic lead carbonate precipitates on the cathode surface, as in the case of an oxygen sensor employing an alkaline electrolyte, so that the electrolytic reduction reaction of oxygen on the cathode surface is hindered. This phenomenon can be prevented by rendering the cathode surface uneven so that the cations which have come to the cathode transferring electric charges are rapidly diffused into the bulk of the electrolyte immediately after completion of the charge supply to the cathode so as not to stay in the vicinity of the cathode surface. In order to render the cathode surface uneven, it is effective to provide grooves on the surface or to attach a screen on the cathode surface.

The present invention is described in more detail with reference to the following examples.

EXAMPLE 1

FIG. 1 shows a cross-sectional view of a galvanic cell type oxygen sensor made in accordance with the present invention. In the figure, 1 is a cathode made up of a platinum disc of a diameter of 5 mm having provided thereon gridlike grooves; 2 is a cyclindrical anode made up of lead; 3 is an electrolyte comprising acetic acid, potassium acetate and lead acetate in amounts of 5 mol/l, 4 mol/l and 0.1 mol/l, respectively; 4 is a hydrophobic diaphragm having a thickness of 20μ made of tetrafluoroethylene-hexafluoropropylene copolymer; 5 is an O-ring for fixing the hydrophobic diaphragm 4 to a cell container 6 made of polyvinyl chloride; 7 is a resistor connected between the cathode 1 and the anode 2; and 8 is a thermistor for temperature compensation. The amount of the electrolyte was 6 ml, the pH of the electrolyte was 6.2, and the resistance of the resistor 7 was 500Ω.

Figure 2:
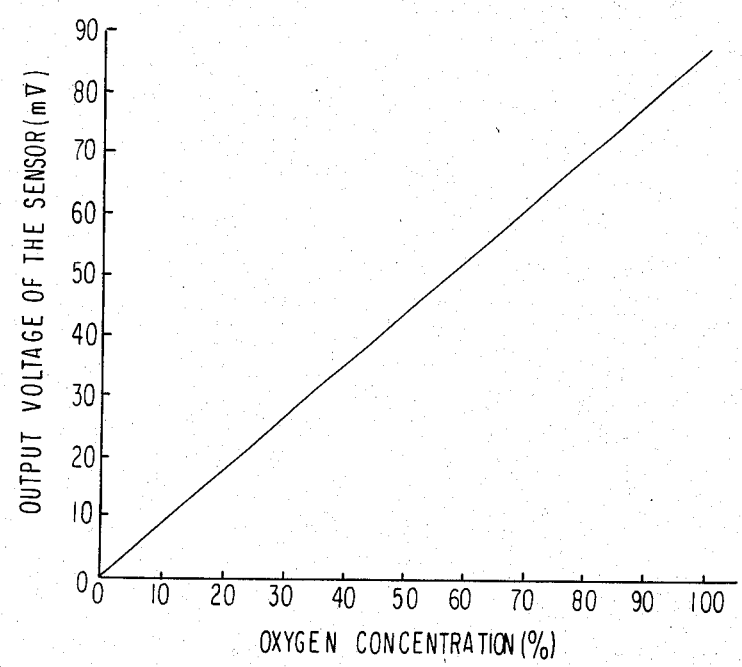
FIG. 2 shows a relation between the output voltage and the oxygen concentration of one embodiment of a galvanic cell type oxygen sensor in accordance with the present invention.

As shown in FIG. 2, there was realized a completely linear relationship between the output voltage and the oxygen concentration of the thus obtained galvanic cell type oxygen sensor.

The comparison in the life was carried out between the thus obtained galvanic cell type oxygen sensor and a conventional galvanic cell type oxygen sensor employing, as an electrolyte, an aqueous solution of potassium hydroxide in an amount of 4 mol/l. The combination of test articles with test conditions is as follows:

A: Conventional type sensor.
  The sensor is placed in air.
B: Conventional type sensor.
  The sensor is placed in a mixed gas atmosphere comprising 10% of carbon dioxide, 21% of oxygen and 69% of nitrogen.
C: Sensor of the invention.
  The sensor is placed in air.
D: Sensor of the invention.

The sensor is placed in a mixed gas atmosphere comprising 10% of carbon dioxide, 21% of oxygen and 69% of nitrogen.

Figure 3:
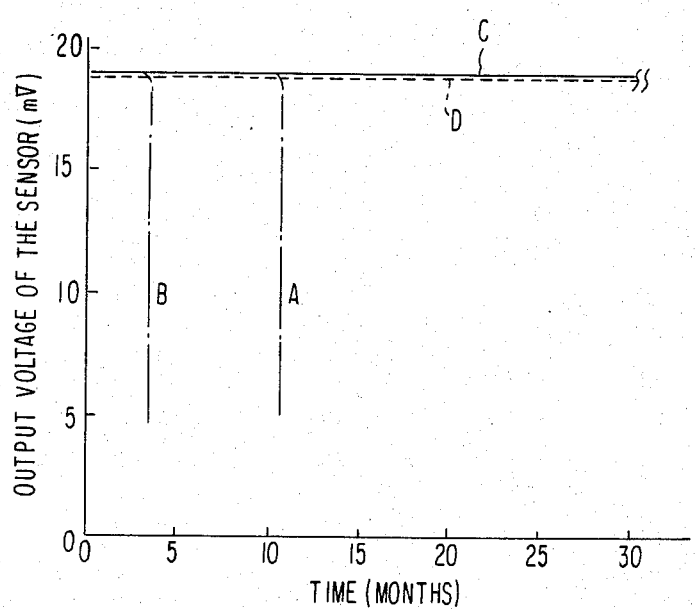
FIG. 3 shows a comparison between the life of the galvanic cell type oxygen sensors of the present invention and that of the conventional galvanic cell type oxygen sensors in terms of changes of output voltages with a lapse of time.

A change of the output voltage with a lapse of time of the respective galvanic cell type oxygen sensor under the above-mentioned test conditions is shown in FIG. 3. It can be ascertained from FIG. 3 that the galvanic cell type oxygen sensors made in accordance with the present invention have a longer life and are never affected by carbon dioxide. Although the sensor samples (C and D) of the present invention continued to be tested for 30 months and the tests were stopped at that time point, it can be fully inferred that the samples have a further life.

EXAMPLE 2

A galvanic cell type oxygen sensor was prepared by the same method as in Example 1 except using as the cathode 1 a titanium disc spot-welded with gold-plated expanded titanium and as the electrolyte 3 an aqueous mixed solution of propionic acid, sodium propionate and lead oxide in amounts of 2 mol/l, 3.5 mol/l and 0.1 mol/l, respectively. When the sensor was placed in a mixed gas atmosphere comprising 80% of carbon dioxide and 20% of oxygen, it showed a stable output for a period longer than 27 months.

EXAMPLE 3

A galvanic cell type oxygen sensor was prepared by the same method as in Example 1 except using as the cathode 1 a gold-plated titanium disc and as the electrolyte 3 an aqueous mixed solution of acetic acid, propionic acid, n-butyric acid, ammonium acetate, potassium n-butyrate and lead oxide in amounts of 0.5 mol/l, 1 mol/l, 1 mol/l, 2 mol/l, 2 mol/l and 0.1 mol/l, respectively. The sensor showed a stable output for 30 months in air.

EXAMPLE 4

Figure 4:
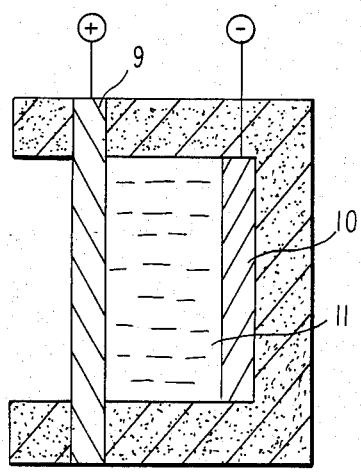
FIG. 4 shows a cross-sectional view of an air-lead cell for the accelerated life test of the sensors.

Because it took too long a time to determine the ultimate life of a galvanic cell type oxygen sensor, an accelerated test for the life of the sensor was carried out with an air-lead cell of such construction as shown in FIG. 4. In other words, as the cathode 9 an air electrode comprising a gas diffusion electrode used in a fuel cell and able to work at a relatively high current density was used; as the anode 10 a lead plate was used; and as the electrolyte 11 an aqueous mixed solution of organic acid, organic acid salt and lead compound, an aqueous solution of potassium hydroxide or an aqueous solution of acetic acid was used, respectively. When the air-lead cell was continuously operated as the current density of 0.3 mA/cm$^2$, a change in the terminal voltage with a lapse of time was evaluated. The working areas of the cathode 9 and the anode 10 were each 10 cm$^2$, and the amount of the electrolyte 11 were 10 ml. The air electrode as the cathode 9 was constructed from three layers comprising a mixture of platinum-supported carbon powders and polytetrafluoroethylene, a current collector made of a metal screen and a porous polytetrafluoroethylene membrane. When an acidic electrolyte was used, a platinum-plated tantalum screen was used as the current collector, and when basic electrolyte was used, a nickel screen was used as the same. In every case, the air-lead cell was operated with natural convection air at room temperature.

Figure 5:
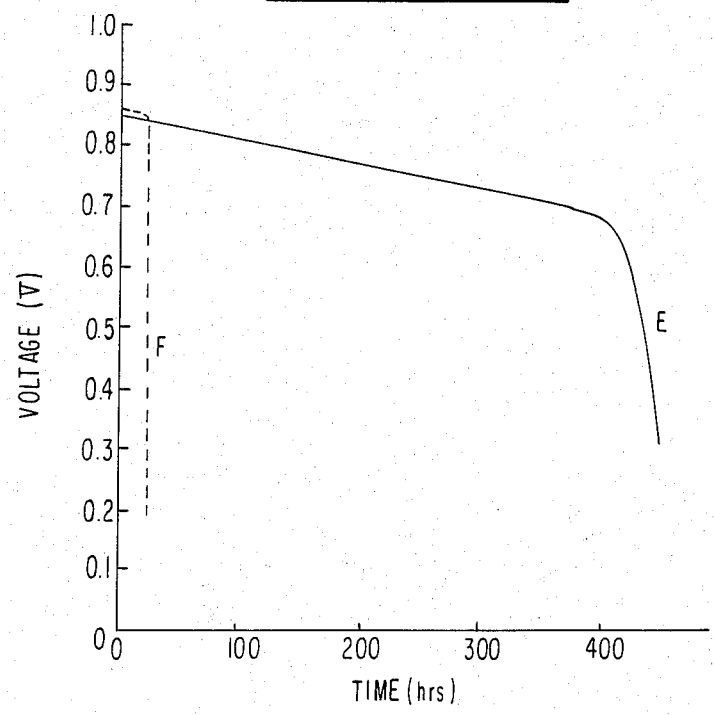
FIG. 5 shows a comparison in the life tests of air-lead cells.

The air-lead cell employing as the electrolyte an aqueous mixed solution of acetic acid, potassium acetate and lead acetate as in Example 1 was referred to as E, and that employing an aqueous solution of potassium hydroxide having a concentration of 4 mol/l as the electrolyte was referred to as F. The results of the life tests of the cell E and F are shown in FIG. 5. It is evident from FIG. 5 that the life of the air-lead cell employing the electrolyte of the present invention is about twenty times that of the one employing the potassium hydroxide solution. The life difference corresponds well to a solubility difference of PbO that is a reaction product of the anode in the both electrolytes, which suggests that the life of a galvanic cell type oxygen sensor made in accordance with the present invention may be twenty times that of the conventional one employing an alkaline hydroxide solution. However, taking into account the life of a galvanic cell type oxygen sensor is actually affected not only by the above-described capacity of the electrolyte but also by water evaporation, it cannot be inferred that the difference between the electrolytes leads to a life difference as large as 20 times. But it can be inferred that the life of the oxygen sensor made in accordance with the present invention is at least several times that of the conventional one.

While the invention has been described in detail and with reference to specific embodiments thereof, it will be apparent to one skilled in the art various changes and modifications can be made therein without departing from the spirit and scope thereof.

What is claimed is:

1. A galvanic cell type oxygen sensor comprising
   (A) a galvanic cell comprising (i) a cathode made up of metal effective for the electrolytic reduction of oxygen, (ii) an anode made up of lead and (iii) an electrolyte comprising an aqueous mixed solution of an organic acid salt and a lead compound, wherein the pH value of said electrolyte is from 4 to 7, and wherein said galvanic cell is so constructed that oxygen diffusion to said cathode is controlled by a polymer film; pg,23
   (B) a resistor; and
   (C) a thermistor
wherein said resistor (B) and thermistor (C) are connected between said cathode and anode.

2. A galvanic cell type oxygen sensor as claimed in claim 1, wherein said organic acid is at least one member selected from the group consisting of acetic acid, propionic acid and n-butyric acid.

3. A galvanic cell type oxygen sensor as claimed in claim 1, wherein said organic acid salt is an alkali metal salt of an organic acid.

4. A galvanic cell type oxygen sensor as claimed in claim 1, wherein said organic acid salt is at least one member selected from the group consisting of formic acid salt, acetic acid salt, propionic acid salt, n-butyric acid salt, maleic acid salt and glutamic acid salt.

* * * * *